(12) United States Patent
Lv et al.

(10) Patent No.: US 10,640,470 B2
(45) Date of Patent: May 5, 2020

(54) QUINAZOLIN CROTYL COMPOUND DIMALEATE CRYSTALS AND PREPARATION METHODS AND USES THEREOF

(71) Applicant: HANGZHOU HUADONG MEDICINE GROUP BIOPHARMACEUTICAL CO. LTD, Hangzhou (CN)

(72) Inventors: Yubin Lv, Hangzhou (CN); Jianming Yin, Hangzhou (CN); Xuehui Huang, Hangzhou (CN); Bangliang Li, Hangzhou (CN)

(73) Assignee: HANGZHOU HUADONG MEDICINE GROUP BIOPHARMACEUTICAL CO. LTD., Hangzhou, Zhejiang (CN)

( * ) Notice: Subject to any disclaimer, the term of this patent is extended or adjusted under 35 U.S.C. 154(b) by 187 days.

(21) Appl. No.: 16/017,084

(22) Filed: Jun. 25, 2018

(65) Prior Publication Data

US 2018/0312472 A1 Nov. 1, 2018

Related U.S. Application Data

(63) Continuation of application No. 15/571,582, filed as application No. PCT/CN2016/080878 on May 3, 2016.

(30) Foreign Application Priority Data

May 5, 2015 (CN) .......................... 2015 1 0226922

(51) Int. Cl.
*C07D 239/94* (2006.01)
*A61P 35/00* (2006.01)
*A61K 31/517* (2006.01)

(52) U.S. Cl.
CPC .......... *C07D 239/94* (2013.01); *A61K 31/517* (2013.01); *A61P 35/00* (2018.01); *C07B 2200/13* (2013.01)

(58) Field of Classification Search
CPC .... C07D 239/94; A61P 35/00; C07B 2200/13
USPC ..................................................... 514/266.4
See application file for complete search history.

(56) References Cited

U.S. PATENT DOCUMENTS

| 10,065,931 B2* | 9/2018 | Lv | A61K 31/517 |
| 2015/0065709 A1* | 3/2015 | Yin | C07D 239/94 |
| | | | 544/284 |
| 2015/0232457 A1* | 8/2015 | Bruns | C07D 405/12 |
| | | | 514/266.24 |

FOREIGN PATENT DOCUMENTS

| CN | 102838550 A | 12/2012 |
| CN | 104151359 A | 11/2014 |
| WO | 2014135876 A1 | 9/2014 |
| WO | WO2020011020 | * 1/2020 |

OTHER PUBLICATIONS

Carmi; Biochemical Pharmacology 84 (2012) 1388-1399. (Year: 2012).*
Extended European Search Report for European Application No. 16789302.3, dated Nov. 16, 2018, 5 pages.
Notification of Reasons for Refusal for Japanese Application No. 2017-558379, dated Sep. 4, 2018, 7 pages.
Decision of Refusal for Japanese Application No. 2017-558379, dated Feb. 5, 2019, 3 pages.
Organic compound crystal preparation handbook—principles and know-how. Edited by Noriaki Hirayama. Maruzen Co., Ltd. Jul. 25, 2008. p. 17-23, 37-40, 45-51, 57-65. Machine Translation included.
The Practice of Medical Chemistry, vol. II. Technomics, Inc. Sep. 25, 1999. p. 347-365. Table 34.1 on p. 349 describes using a compound in the form of a maleate and to use ethyl acetate as a solvent (see p. 2 of attached Notification of Reasons for Refusal for Japanese Application No. 2017-558379).
Solvent Handbook. Teruzo Asahara. Kodansha, Ltd. 1985. p. 47-51. Table 3.3 on p. 49 describes using a compound in the form of a maleate and to use ethyl acetate as a solvent (see p. 2 of attached Notification of Reasons for Refusal for Japanese Application No. 2017-558379).
International Search Report for International Application No. PCT/CN2016/080878, dated Aug. 8, 2016, 4 pages.

* cited by examiner

*Primary Examiner* — Daniel R Carcanague
(74) *Attorney, Agent, or Firm* — Armstrong Teasdale LLP

(57) ABSTRACT

Disclosed are crystal forms K, E, F and G of the dimaleate of the compound as shown in formula I, and preparation methods and uses thereof. The crystal forms K, E, F and G have superior storage stability and solubility, so that they are more suitable for being used as the drug substance for drug product preparations.

12 Claims, 11 Drawing Sheets

QUINAZOLIN CROTYL COMPOUND DIMALEATE CRYSTALS AND PREPARATION METHODS AND USES THEREOF

CROSS-REFERENCE TO ADDITIONAL APPLICATIONS

This application is a continuation of U.S. application Ser. No. 15/571,582 filed on Nov. 3, 2017 (now allowed), which was the national stage entry of PCT/CN2016/080878 filed on May 3, 2016, which claims priority to CN 201510226922.9 filed on May 5, 2015, all of which are incorporated by reference in their entirety for all purposes.

TECHNICAL FIELD

The present invention relates to the crystals of quinazolin crotyl compound dimaleate and preparation methods and uses thereof.

TECHNICAL BACKGROUND

Patent document CN102838550A discloses a quinazolin crotyl compound-a compound of formula I,

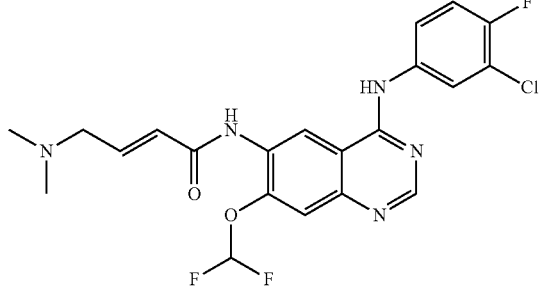

The compound of formula I has been proved to be the ideal and highly effective dual irreversible tyrosine kinase inhibitor, it can competitively bind to ATP by acting on the intracellular part of EGFR, inhibit the activation and phosphorylation of kinase, and block EGFR tyrosine kinase ATP binding sites so as to achieve the purpose of specific inhibition of EGFR. The compound can be used for the treatment or prevention of various indications related to EGFR and HER2 kinase function, comprising but are not limited to breast cancer, ovarian cancer, gastrointestinal cancer, esophageal cancer, lung cancer, head and neck squamous cell carcinoma, pancreatic cancer, epidermal squamous carcinoma, prostate cancer, glioma and nasopharyngeal carcinoma and other malignant tumor diseases.

The example 1 of the above-mentioned patent document also discloses a method for the synthesis of the compound of the above formula I, which provides a free base of the compound of formula I. The inventors have found that the long-term storage stability and the water solubility of the free base are poor, thus the free base is not ideal for use as drug substance for drug product preparations.

Accordingly, there is a need for drug substance of the compound of formula I having better physical properties and is suitable for use in pharmaceutical applications.

SUMMARY OF THE INVENTION

The inventors prepared a variety of crystal forms of various salts of the compound of formula I and studied the physicochemical properties and stabilities of these crystal forms. The inventors have found that the crystal form K, crystal form G, crystal form E and crystal form F of the dimaleate of the compound of formula I have unexpectedly good effects in terms of storage stability and water solubility, in which the crystal form K and the crystal form F are especially suitable for use as drug substance for drug product preparations.

Accordingly, it is an object of the present invention to provide a crystal form K, crystal form G, crystal form E and crystal form F of the dimaleate of the compound of formula I and preparation methods and uses thereof.

The present invention provides a crystal form K of the dimaleate of the compound of formula I,

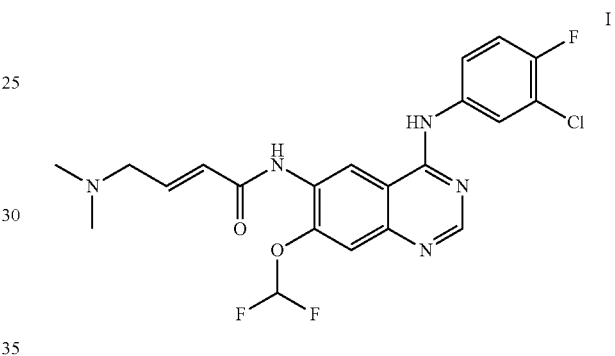

The X-ray powder diffraction pattern (CuKα radiation) of the crystal form K has characteristic peaks at the following diffraction angles 2θ: 5.8±0.2°, 12.5±0.2°, 14.8±0.2°, 18.9±0.2°, 21.7±0.2°, 23.6±0.2°, 24.9±0.2° and 25.8±0.2°.

Preferably, the X-ray powder diffraction pattern (CuKα radiation) of the crystal form K has characteristic peaks at the above diffraction angles 2θ, and the relative intensities are as follows:

| Diffraction angles 2θ | Relative intensities (%) |
|---|---|
| 5.8 ± 0.2° | 53.8 |
| 12.5 ± 0.2° | 83.9 |
| 14.8 ± 0.2° | 69.4 |
| 18.9 ± 0.2° | 86.1 |
| 21.7 ± 0.2° | 100.0 |
| 23.6 ± 0.2° | 80.0 |
| 24.9 ± 0.2° | 90.0 |
| 25.8 ± 0.2° | 77.2 |

Preferably, the X-ray powder diffraction pattern (CuKα radiation) of the crystal form K of the dimaleate of the compound of formula I further has characteristic peaks at the following diffraction angles 2θ: 17.4±0.2°, 18.0±0.2°, 20.3±0.2°, 24.3±0.2°, 26.4±0.2°, 27.3±0.2°, 28.3±0.2° and 31.7±0.2°.

Preferably, the X-ray powder diffraction pattern (CuKα radiation) of the crystal form K of the dimaleate of the compound of formula I has characteristic peaks at the above diffraction angles 2θ, and the relative intensities are as follows:

| Diffraction angles 2θ | Relative intensities (%) |
| --- | --- |
| 17.4 ± 0.2° | 43.0 |
| 18.0 ± 0.2° | 61.0 |
| 20.3 ± 0.2° | 44.2 |
| 24.3 ± 0.2° | 44.3 |
| 26.4 ± 0.2° | 40.6 |
| 27.3 ± 0.2° | 59.3 |
| 28.3 ± 0.2° | 53.7 |
| 31.7 ± 0.2° | 43.7. |

Preferably, the X-ray powder diffraction pattern (CuKα radiation) of the crystal form K of the dimaleate of the compound of formula I further has characteristic peaks at the following diffraction angles 2θ: 21.1±0.2°, 22.7±0.2°, 29.2±0.2°, 30.3±0.2°, 32.7±0.2°, 33.1±0.2°, 36.5±0.2° and 38.3±0.2°.

Preferably, the X-ray powder diffraction pattern (CuKα radiation) of the crystal form K of the dimaleate of the compound of formula I has characteristic peaks at the above diffraction angles 2θ, and the relative intensities are as follows:

| Diffraction angles 2θ | Relative intensities (%) |
| --- | --- |
| 21.1 ± 0.2° | 23.3 |
| 22.7 ± 0.2° | 40.0 |
| 29.2 ± 0.2° | 28.9 |
| 30.3 ± 0.2° | 17.7 |
| 32.7 ± 0.2° | 30.7 |
| 33.1 ± 0.2° | 38.9 |
| 36.5 ± 0.2° | 17.1 |
| 38.3 ± 0.2° | 27.1. |

Unrestrictively, the crystal form K of the dimaleate of the compound of formula I has an X-ray powder diffraction pattern substantially shown as FIG. 3.

Further, the melting point of the crystal form K is 109.4±2° C.

Further, the crystal form K of the present invention shows an absorption peak in the thermogram determined by differential scanning calorimetry (DSC), and the position of the absorption peak is at 127±2° C.

Unrestrictively, the crystal form K of the dimaleate of the compound of formula I has a thermogravimetric analysis (TGA) thermogram substantially shown as FIG. 4.

Unrestrictively, the crystal form K of the dimaleate of the compound of formula I has a differential thermal scanning (DSC) thermogram substantially shown as FIG. 5.

The present invention also provides a preparation method for the crystal form K of the dimaleate of the compound of formula I, comprising the following steps:

(1) mixing the free base of the compound of formula I with ethyl acetate, and heating the mixture to 40-60° C.;

(2) slowly adding the ethyl acetate solution of maleic acid to the mixture obtained in the step (1) until precipitation appears, adding deionized water:

(3) adding the ethyl acetate solution of maleic acid to the reaction system obtained in the step (2), to heating and stirring the newly obtained system, cooling and crystallizing, separating the crystals to obtain said crystal form K.

Wherein the free base of the compound of formula I can be synthesized according to an existing method, for example, the method disclosed in example 1 of patent document CN 102838550A.

In the method of the present invention, the molar ratio of the free base of the compound of formula I to the maleic acid is 1:(1.95–2.05), preferably 1:2. Wherein the amount of maleic acid is the sum of the amounts of maleic acid used in step (2) and step (3).

In step (1), the mixture is preferably heated to 45-55° C.

Preferably, the concentration of the free base of the compound of formula I is from 0.5 to 1.5 g/mL in the mixture of the free base of the compound of formula I and ethyl acetate in step (1).

Preferably, in step (2), the ethyl acetate solution of maleic acid is added dropwise.

Preferably, the concentrations of the ethyl acetate solution of maleic acid in steps (2) and (3) may be the same or different and the concentrations are 0.05 to 0.5 mol/L.

In the method of the present invention, the volume ratio of the deionized water to ethyl acetate is (0.01–0.02):1. The ethyl acetate herein includes the total amount of ethyl acetate used in steps (1) to (3).

In step (3), the addition rate of the ethyl acetate solution of maleic acid is preferably 0.5 to 2 mL/min. The solution may be added in any suitable manner, for example through a syringe.

Preferably, in step (3), the heating temperature is 40-60° C., and the stirring time is 10 to 20 hours.

Preferably, in step (3), the temperature is preferably cooled to 5-30° C., more preferably to room temperature.

In step (3), the separation may employ conventional separation methods in organic chemistry, such as filtration, centrifugation, and the like.

The present invention also provides a crystal form E of the dimaleate of the compound of formula I.

The X-ray powder diffraction pattern (CuKα radiation) of the crystal form E has characteristic peaks at the following diffraction angles 2θ: 4.5±0.2°, 12.0±0.2°, 18.2±0.2°, 19.8±0.2°, 20.6±0.2°, 21.9±0.2°, 24.7±0.2°, and 25.3±0.2°.

Preferably, for the X-ray powder diffraction pattern (CuKα radiation) of the crystal form E, the relative intensities of the characteristic peaks at the above diffraction angles 2θ are as follows:

| Diffraction angles 2θ | Relative intensities (%) |
| --- | --- |
| 4.5 ± 0.2° | 26.3 |
| 12.0 ± 0.2° | 14.1 |
| 18.2 ± 0.2° | 82.3 |
| 19.8 ± 0.2° | 31.2 |
| 20.6 ± 0.2° | 27.7 |
| 21.9 ± 0.2° | 50.8 |
| 24.7 ± 0.2° | 34.5 |
| 25.3 ± 0.2° | 100.0. |

Unrestrictively, the crystal form E of the dimaleate of the compound of formula I has an X-ray powder diffraction pattern substantially shown as FIG. 6.

Unrestrictively, the crystal form E of the dimaleate of the compound of formula I has a thermogravimetric analysis (TGA) thermogram substantially shown as FIG. 7.

Unrestrictively, the crystal form E of the dimaleate of the compound of formula I has a differential thermal scanning (DSC) thermogram substantially shown as FIG. 8.

The present invention also provides a preparation method for the crystal form E, comprising the following steps:

(1) mixing the compound of formula I with ethyl acetate, and stirring the mixture:

(2) adding the ethyl acetate solution of maleic acid to the mixture obtained in the step (1), stirring the new mixture to obtain the crystal form E of the dimaleate of the compound of formula I.

The present invention also provides a crystal form F of the dimaleate of the compound of formula I.

The X-ray powder diffraction pattern (CuKα radiation) of the crystal form F has characteristic peaks at the following diffraction angles 2θ: 5.1±0.2°, 11.5±0.2°, 17.5±0.2°, 18.7±0.2°, 19.7±0.2°, 23.3±0.2°, 25.0±0.2°, and 26.2±0.2°.

Preferably, for the X-ray powder diffraction pattern (CuKα radiation) of the crystal form F, the relative intensities of the characteristic peaks at the above diffraction angles 2θ are as follows:

| Diffraction angles 2θ | Relative intensities (%) |
| --- | --- |
| 5.1 ± 0.2° | 100.0 |
| 11.5 ± 0.2° | 20.5 |
| 17.5 ± 0.2° | 14.2 |
| 18.7 ± 0.2° | 42.8 |
| 19.7 ± 0.2° | 22.5 |
| 23.3 ± 0.2° | 31.0 |
| 25.0 ± 0.2° | 44.6 |
| 26.2 ± 0.2° | 42.1. |

Unrestrictively, the crystal form F of the dimaleate of the compound of formula I has an X-ray powder diffraction pattern substantially shown as FIG. 9.

Unrestrictively, the crystal form F of the dimaleate of the compound of formula I has a thermogravimetric analysis (TGA) thermogram substantially shown as FIG. 10.

Unrestrictively, the crystal form F of the dimaleate of the compound of formula I has a differential thermal scanning (DSC) thermogram substantially shown as FIG. 11.

The present invention also provides a preparation method for the crystal form F, comprising adding crystal form E into an alcoholic solvent, stirring the obtained mixture, volatilizing the solvent or adding anti-solvent to obtain crystal form F. Above mentioned alcoholic solvent is preferably ethanol.

The present invention also provides a crystal form G of the dimaleate of the compound of formula I.

The X-ray powder diffraction pattern (CuKα radiation) of the crystal form G has characteristic peaks at the following diffraction angles 2θ: 4.5±0.2°, 10.1±0.2°, 15.1±0.2°, 18.5±0.2°, 25.8±0.2°.

Preferably, for the X-ray powder diffraction pattern (CuKα radiation) of the crystal form G the relative intensities of the characteristic peaks at the above diffraction angles 2θ are as follows:

| Diffraction angles 2θ | Relative intensities (%) |
| --- | --- |
| 4.5 ± 0.2° | 28.8 |
| 10.1 ± 0.2° | 19.5 |
| 15.1 ± 0.2° | 13.2 |
| 18.5 ± 0.2° | 38.1 |
| 25.8 ± 0.2° | 100.0. |

The X-ray powder diffraction pattern (CuKα radiation) of the crystal form G further has characteristic peaks at the following diffraction angles 2θ: 21.4±0.2° and 27.4±0.2°. Preferably, for the X-ray powder diffraction pattern (CuKα radiation) of the crystal form G of the dimaleate of the compound of formula I, the relative intensities at the above-described characteristic peaks are:

| 21.4 ± 0.2° | 1.21 |
| --- | --- |
| 27.4 ± 0.2° | 3.5. |

Unrestrictively, the crystal form G of the dimaleate of the compound of formula I has an X-ray powder diffraction pattern substantially shown as FIG. 12.

Unrestrictively, the crystal form G of the dimaleate of the compound of formula I has a thermogravimetric analysis (TGA) thermogram substantially shown as FIG. 13.

Unrestrictively, the crystal form G of the dimaleate of the compound of formula I has a differential thermal scanning (DSC) thermogram substantially shown as FIG. 14.

The present invention also provides a preparation method for the crystal form G comprising adding crystal form E into a ketone solvent, stirring the obtained mixture, volatilizing the solvent or adding anti-solvent to obtain crystal form G.

Above mentioned ketone solvent is preferably acetone.

It should be noted that the relative intensity values of the characteristic peaks of the crystal form K, the crystal form E, the crystal form F, and the crystal form G are only measured in some embodiments of the present invention and are not absolute. A person skilled in the field will understand that due to preferred orientation, the relative intensity of the same crystal form will vary under different test conditions (e.g. measuring instruments, methods, operations, etc.).

The relative intensities of the characteristic peaks of the above crystal forms may fluctuate within a certain range, for example within the range of ±10%. In other cases, the relative intensity values of the characteristic peaks of the above crystal form can fluctuate in a wider range.

The crystal form K, crystal form E, crystal form F and crystal form G of the present invention are substantially pure crystals, i.e. crystals which are substantially free of other crystal forms.

The present invention also provides a composition comprising at least one of the crystal form K, crystal form G crystal form E or crystal form F of the dimaleate of the compound of formula I.

The present invention also provides the use of the crystal form K, crystal form G, crystal form E or crystal form F of the dimaleate of the compound of formula I in preparation of a medicament for the prevention or treatment of indications associated with EGFR and HER2 kinase function, including but are not limited to breast cancer, ovarian cancer, gastrointestinal cancer, esophageal cancer, lung cancer, head and neck squamous cell carcinoma, pancreatic cancer, epidermal squamous carcinoma, prostate cancer, glioma and nasopharyngeal cancer and other malignant tumor diseases.

Compared with the free base of the compound of formula I prepared with the current method and the other crystal forms of the compound of formula I obtained by the test of the applicant of the present invention, the crystal form K, crystal form G, crystal form E or crystal form F of the dimaleate of the compound of formula I of the present invention have excellent storage stability and solubility, and are more suitable for use as drug substance for drug product preparation.

EMBODIMENTS

The technical solution of the present invention will be further illustrated with the combination of the examples. It should be understood that these examples are provided for illustrating the basic principle, the essential features and advantages of the present invention, the specific implementing conditions employed in the examples may be adjusted within the scope of the present field, and that the protection scope of the invention is not limited by the examples.

In the following examples, the XRPD of the crystal form was determined using a PANalytical Empyrean X-ray powder diffraction analyzer, the parameters are summarized in Table 1.

TABLE 1

| | Reflection parameters |
|---|---|
| X-ray | Cu, kα, |
| | Kα1 (Å): 1.540598; Kα2 (Å): 1.544426 |
| | Kα2/Kα1 intensity ratio: 0.50 |
| X-ray tube setting | 45 kV, 40 mA |
| Divergence slit | Automatic |
| Monochromator | Non |
| Scanning model | Continuous |
| Scanning range (°2TH) | 3°~40° |

TABLE 1-continued

| | Reflection parameters |
|---|---|
| Scanning step length (°2TH) | 0.017 |
| Scanning time (min) | About 4 min |

The DSC thermograms were collected by TA Q200 and TA Q2000 differential scanning calorimeters. The TGA thermograms were collected by TA Q500 and TA Q5000 thermogravimetric analyzers. The scanning parameters are summarized in Table 2.

TABLE 2

| | TGA | DSC |
|---|---|---|
| Sample plate | Platinum pan, open | Aluminum pan, with a cover pressed on the pan |
| Temperature range (° C.) | 30-300° C. | 25-250° C. |
| Scanning speed (° C./min) | 10 | 10 |
| Shield gas | Nitrogen | Nitrogen |

In the following examples, the free base of the compound of formula I was prepared according to the method described in example 1 of the patent document CN 102838550A.

In the following examples, the conditions that are not specified are the conditions in conventional experiment.

Example 1 Preparation and Characterization of the Crystal Form K of the Dimaleate of the Compound of Formula I 13.5 g of the free base of the compound of formula I was weighed and was placed in a 500-mL three-necked flask, 15 mL of ethyl acetate was added, the mixture was mechanically stirred and was heated to 50° C. It can be observed that the solution was turbid, 0.2 mol/L of ethyl acetate solution of maleic acid was added dropwise until precipitation appeared (about 80 mL was added), to then 3 mL of deionized water was added, then 0.2 mol/L of ethyl acetate solution of maleic acid was added with a syringe at a rate of 1 mL/min, about 112 mL was added, the mixture was stirred for 15 hours with the temperature kept at about 50° C., then the temperature was decreased naturally to room temperature, suction filtration was carried out and the obtained product was dried under vacuum at 35° C. for 5 hours to obtain the crystal form K of the dimaleate of the compound of formula I with a HPLC purity of 99.3%.

Figure 1:
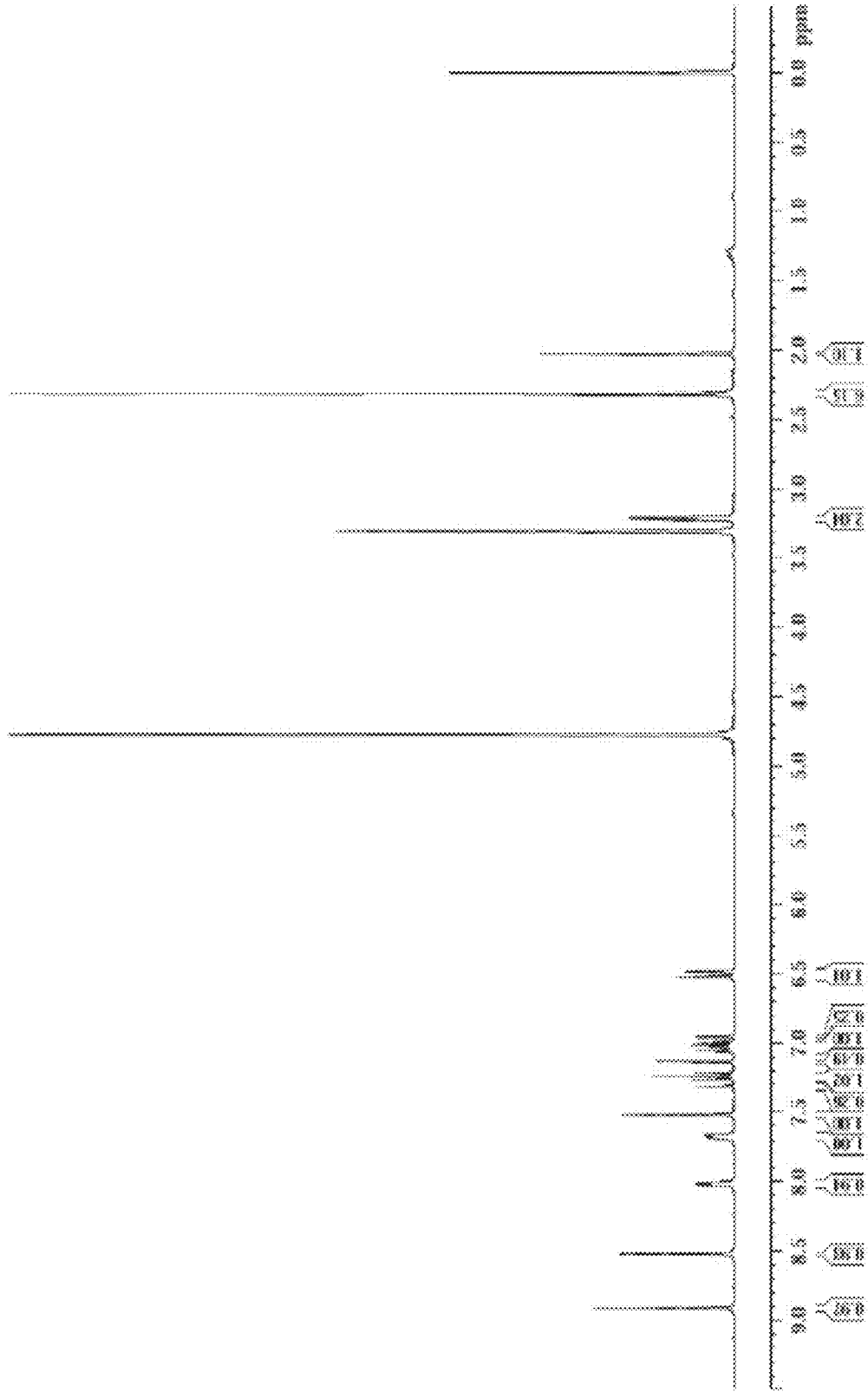
FIG. 1 is the NMR spectrum of the free base of the compound of formula I.
Figure 2:
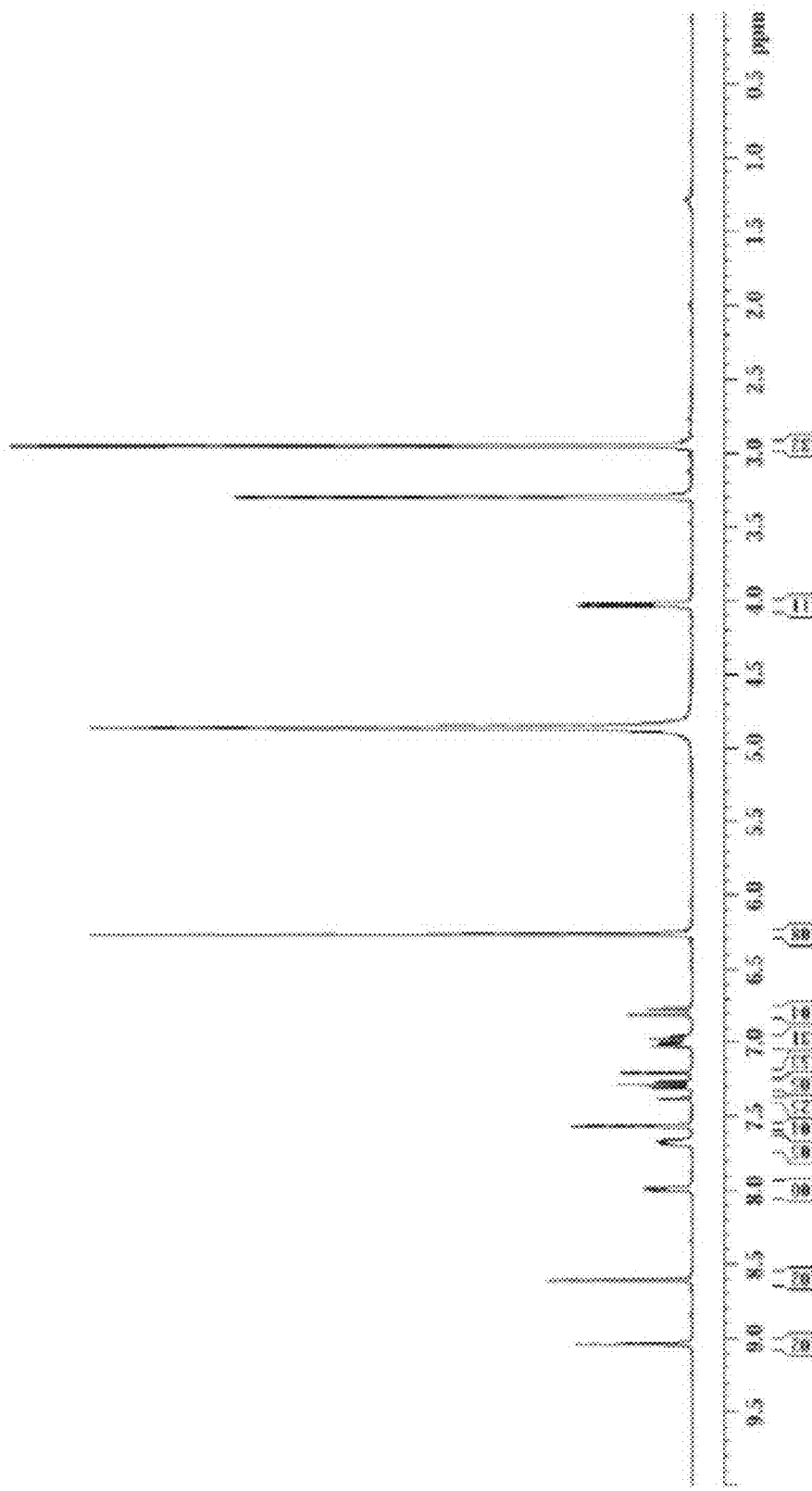
FIG. 2 is the NMR spectrum of the crystal form K.

The free base of the compound of formula I and the obtained crystal form K were subjected to a nuclear magnetic test, and the solvent was MeOD, the NMR spectra as shown in FIGS. 1 and 2, respectively. From the results of liquid nuclear magnetic resonance, the chemical shift of the two hydrogen atoms on the vinyl group of maleic acid was about 6.3 ppm, the integral area was defined as 1.0, the chemical shift of one H on the free base was about 8.6 ppm, the integral area was 0.25, and the stoichiometric ratio of the hydrogen of the free base to the hydrogen of the vinyl group on maleic acid was 1:4. Since there were two hydrogen atoms on the vinyl group, the free base of the compound of formula I and the maleic acid formed a salt according to a stoichiometric ratio of 1:2, thus proving that the crystal form K was the dimaleate of the compound of formula I.

Figure 3:
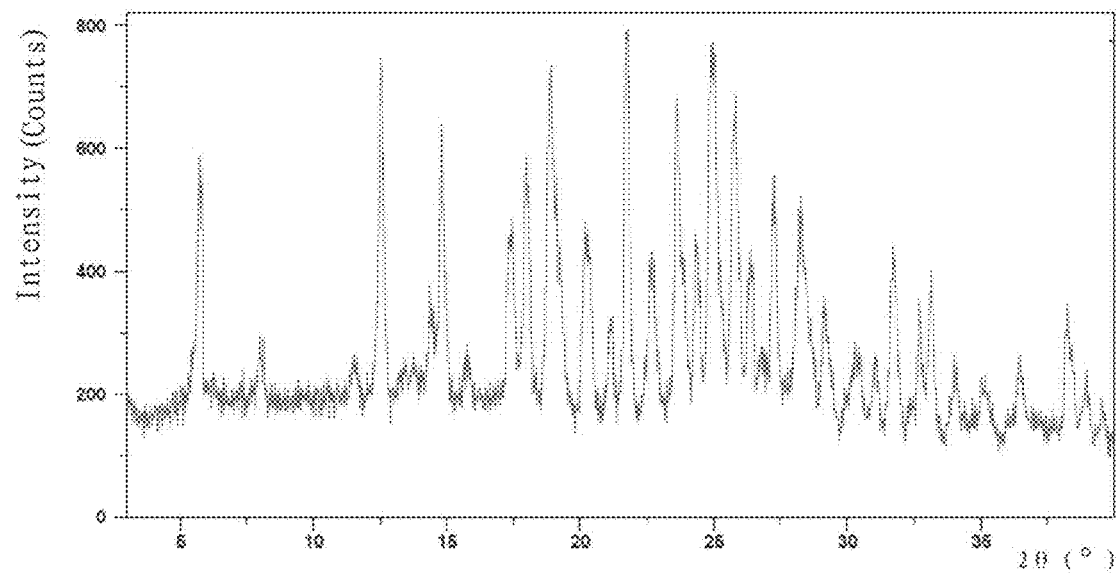
FIG. 3 is the XRPD pattern of the crystal form K.
Figure 4:
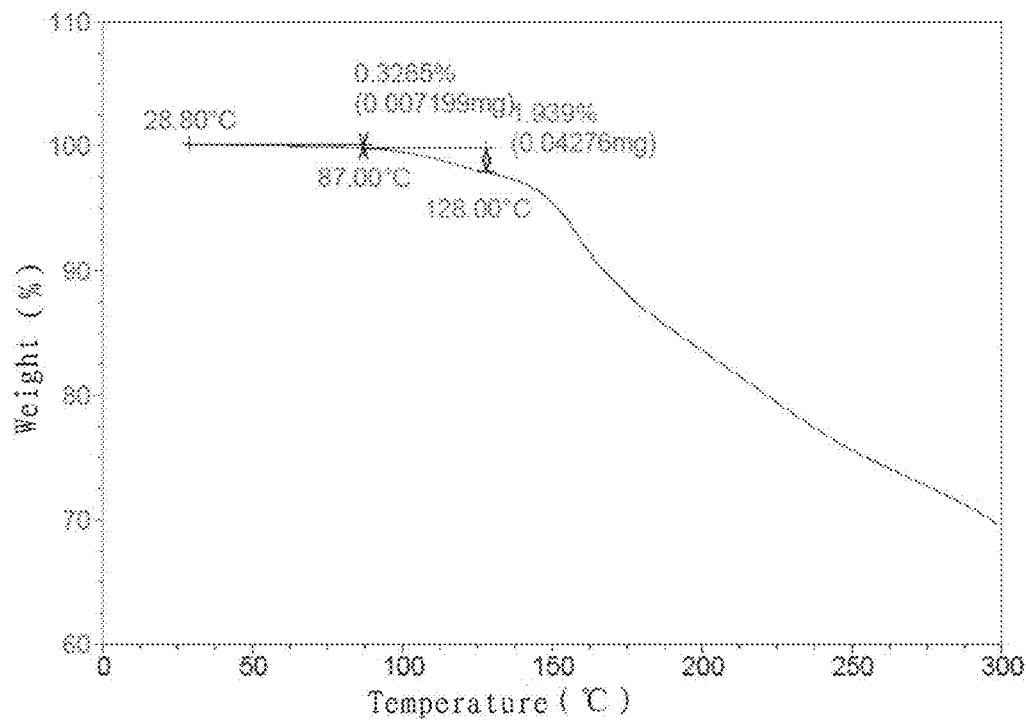
FIG. 4 is the TGA thermogram of the crystal form K.
Figure 5:
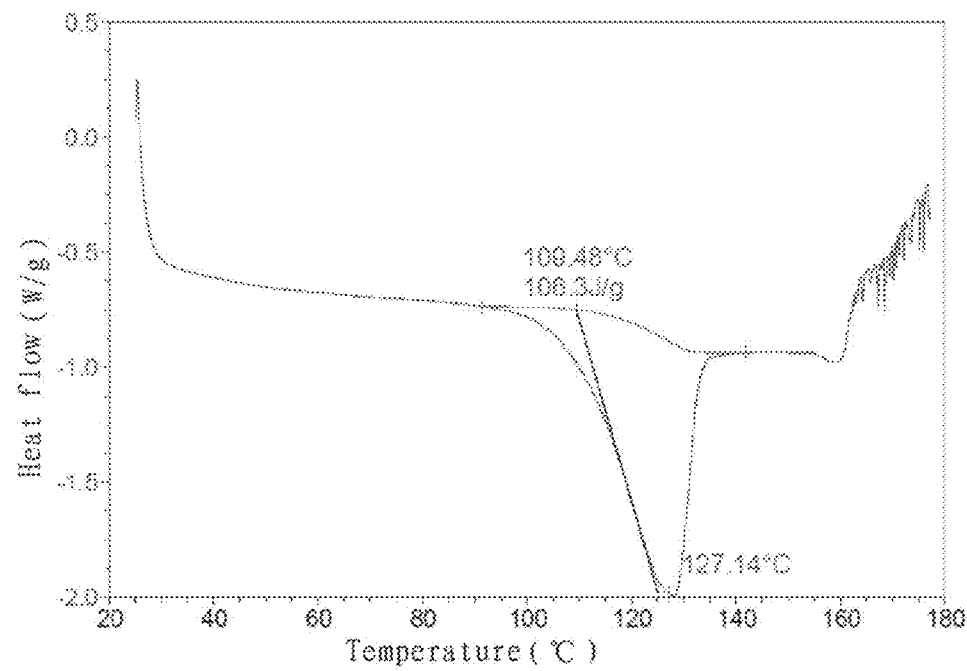
FIG. 5 is the DSC thermogram of the crystal form K.

The crystal form K was subjected to X-ray powder diffraction analysis (XRPD), thermogravimetric analysis (TGA) and differential thermal analysis (DSC). The experimental results are shown in FIGS. 3-5.

DSC showed that the melting point of crystal form K was 109.48° C. and an absorption peak appeared at 127±2° C.

TGA showed that the crystal form K had two steps of weight loss, the weight losses were 0.3% and 1.9%, respectively.

Example 2 Preparation and Characterization of the Crystal Form E of the Dimaleate of the Compound of Formula I 300.6 mg of the free base of the compound of formula I was added to a 20-mL glass vial, 4 mL ethyl acetate was added thereto. The mixture was stirred at 50° C. for 5 minutes. 6.6 mL of 0.2 mol/L of ethyl acetate solution of maleic acid was added thereto, the reaction was carried out under stirring at 50° C. for 24 hours to obtain the crystal form E of the dimaleate of the compound of formula I.

The crystal form E was subjected to a nuclear magnetic test, the NMR spectrum of the crystal to form E was similar to the NMR spectrum of the crystal form K of example 1, proving that the crystal form E was the dimaleate of the compound of formula I.

Figure 6:
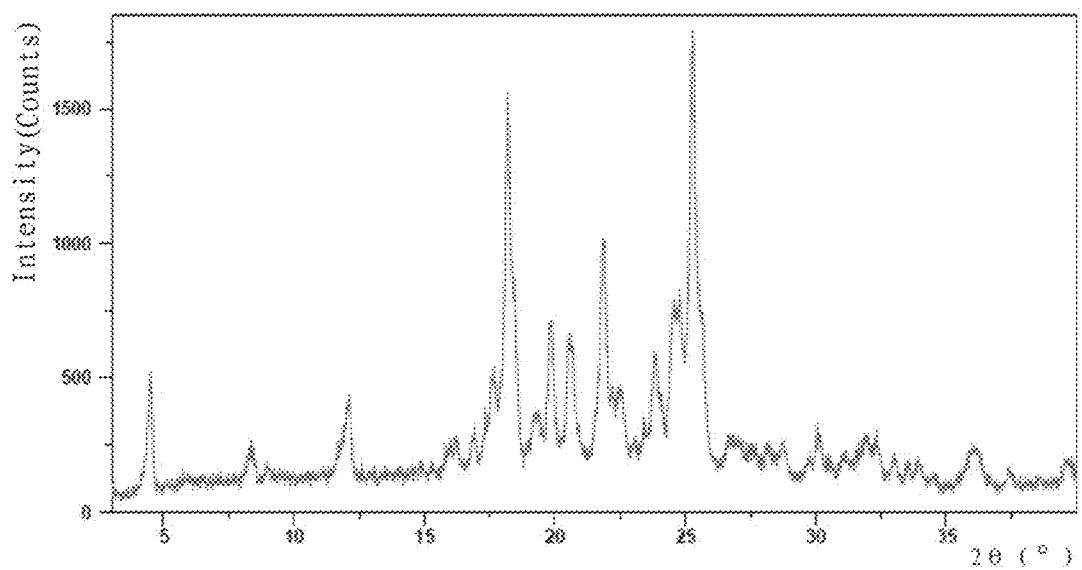
FIG. 6 is the XRPD pattern of the crystal form E.
Figure 7:
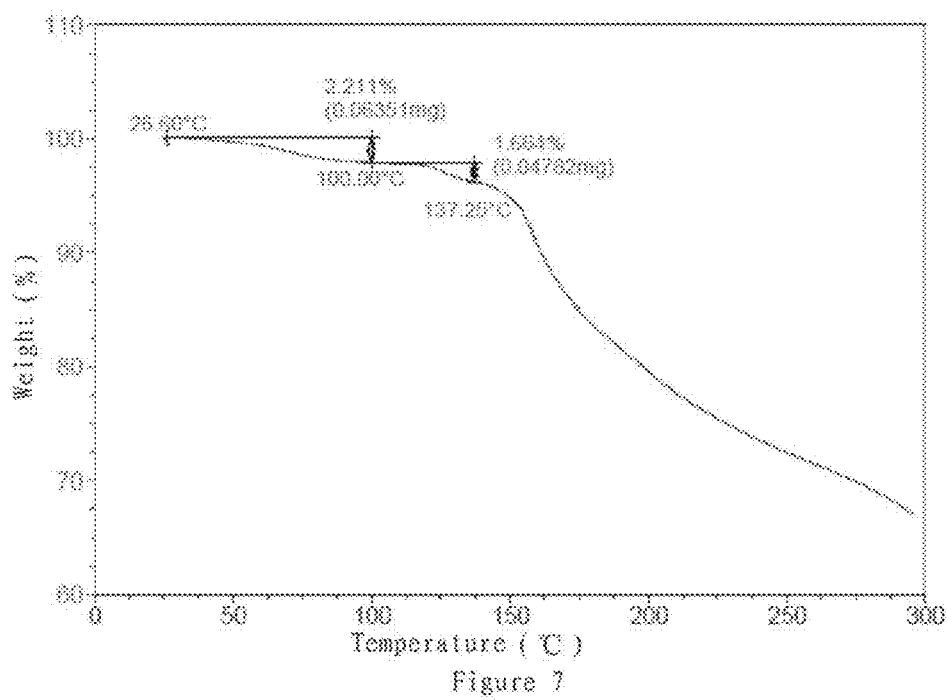
FIG. 7 is the TGA thermogram of the crystal form E.
Figure 8:
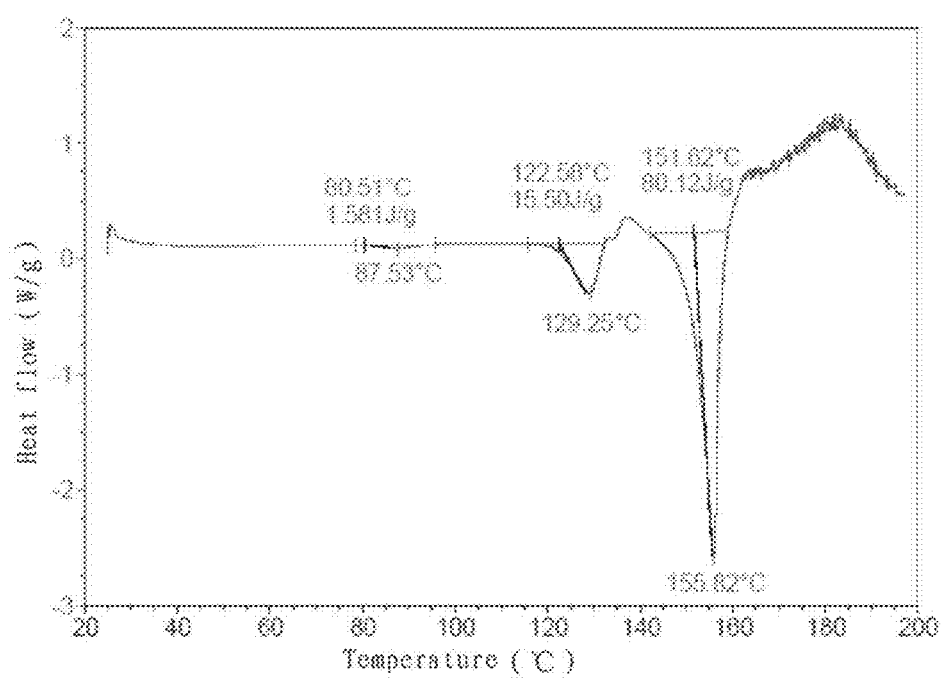
FIG. 8 is the DSC thermogram of the crystal form E.

The experiment results of X-ray powder diffraction analysis (XRPD), thermogravimetric analysis (TGA) and differential thermal analysis (DSC) of crystal form E are shown in FIGS. 6-8.

Example 3 Preparation and Characterization of the Crystal Form F of the Dimaleate of the Compound of Formula I 8.3 mg of the crystal form E of the dimaleate of the compound of formula I was added to a 3-mL glass vial, 0.5 mL ethanol was added, the mixture was heated to 60° C. for the crystal to be completely dissolved to obtain a clear solution. The temperature of the obtained clear solution was quickly decreased to 5° C., the solid was separated out, centrifuged to obtain crystal form F.

The crystal form F was subjected to a nuclear magnetic test, the NMR spectrum of the crystal form F was similar to the NMR spectrum of the crystal form K of example 1, proving that the crystal form F was the dimaleate of the compound of formula I.

Figure 9:
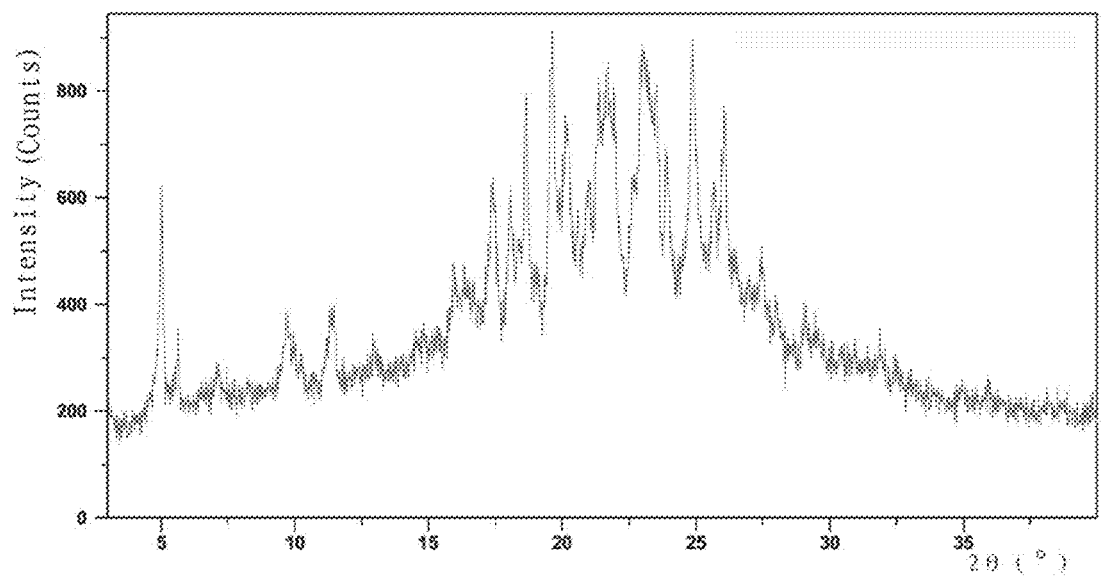
FIG. 9 is the XRPD pattern of the crystal form F.
Figure 10:
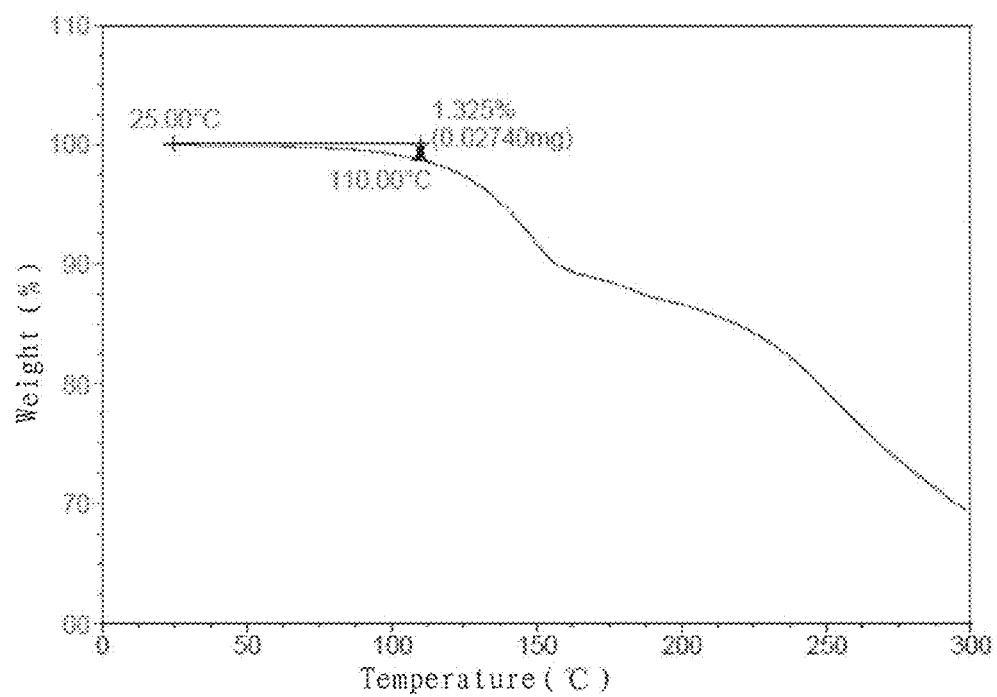
FIG. 10 is the TGA thermogram of the crystal form F.
Figure 11:
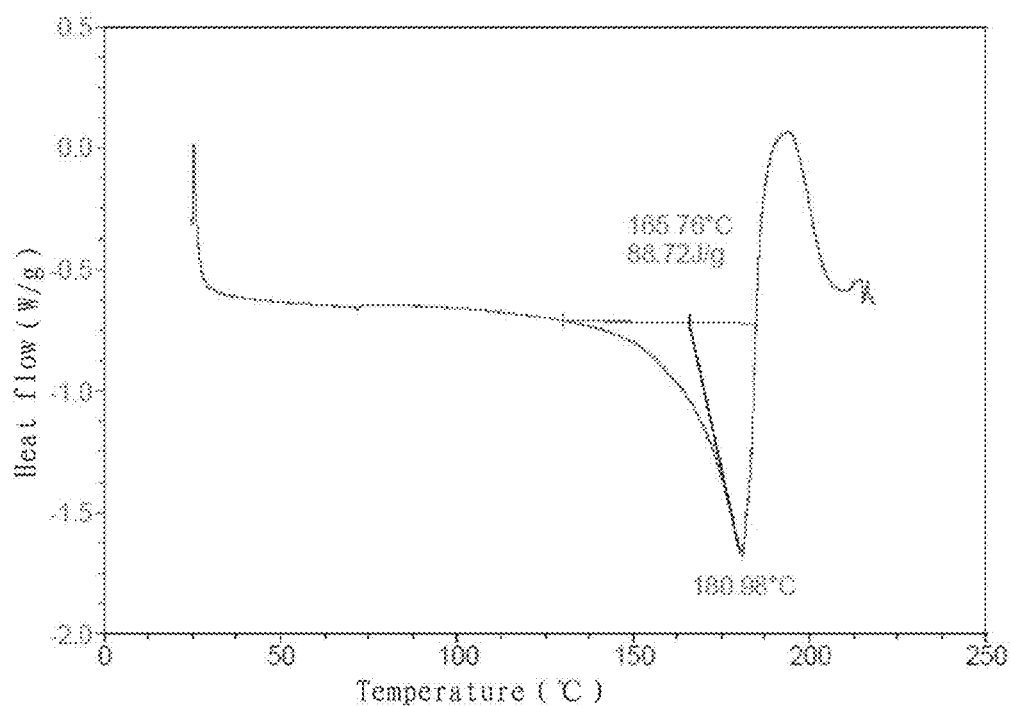
FIG. 11 is the DSC thermogram of the crystal form F.

The experiment results of X-ray powder diffraction analysis (XRPD), thermogravimetric analysis (TGA) and differential thermal analysis (DSC) of the crystal form F are shown in FIGS. 9-11.

It can be known from the DSC thermogram and the TGA thermogram that the melting point of crystal form F was 155.6° C., the enthalpy value was 108.1 J/g, and the weight loss was 0.4%.

Example 4 Preparation and Characterization of the Crystal Form G of the Dimaleate of the Compound of Formula I 11.3 mg of the crystal form E of the dimaleate of the compound of formula I was added to a 20-mL glass vial, 1.9 mL acetone was added, the crystal was completely dissolved after oscillation, the anti-solvent n-heptane was added dropwise under stirring until there's solid separated out, the solid was centrifuged to obtain crystal form G.

The crystal form G was subjected to a nuclear magnetic test, the NMR spectrum of the crystal form G was similar to the NMR spectrum of the crystal form K of example 1, proving that the crystal form G was the dimaleate of the compound of formula I.

Figure 12:
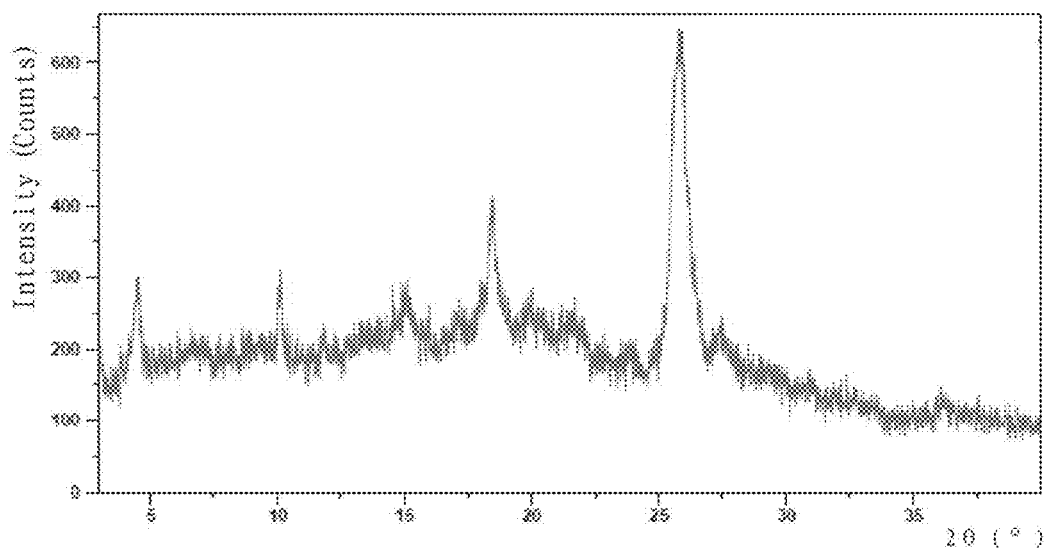
FIG. 12 is the XRPD pattern of the crystal form G.
Figure 13:
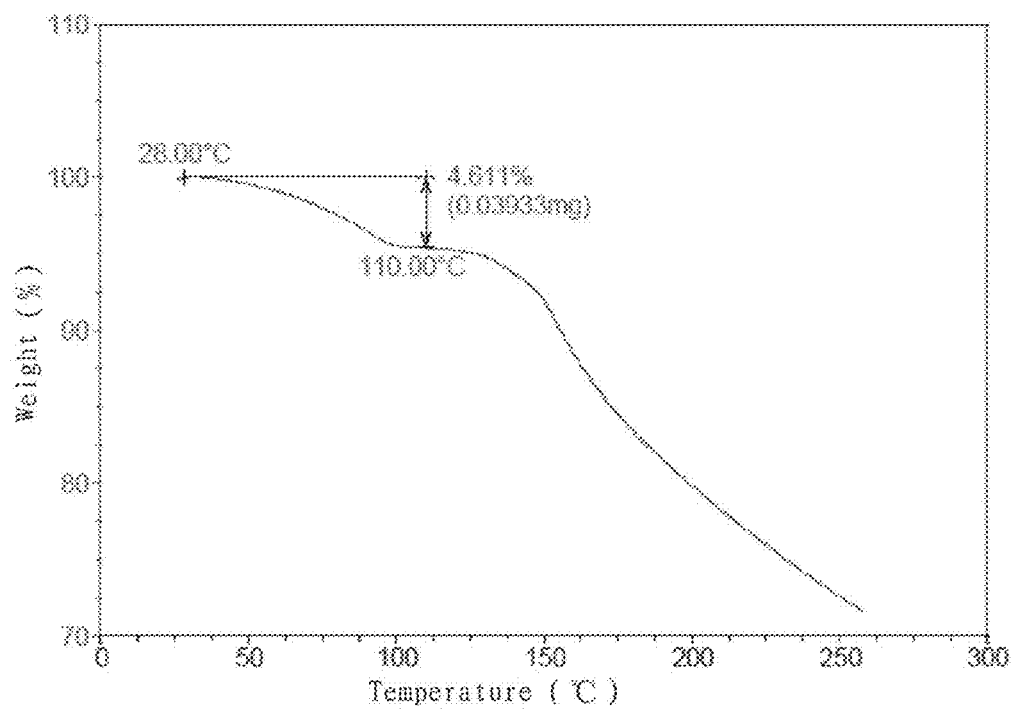
FIG. 13 is the TGA thermogram of the crystal form G.
Figure 14:
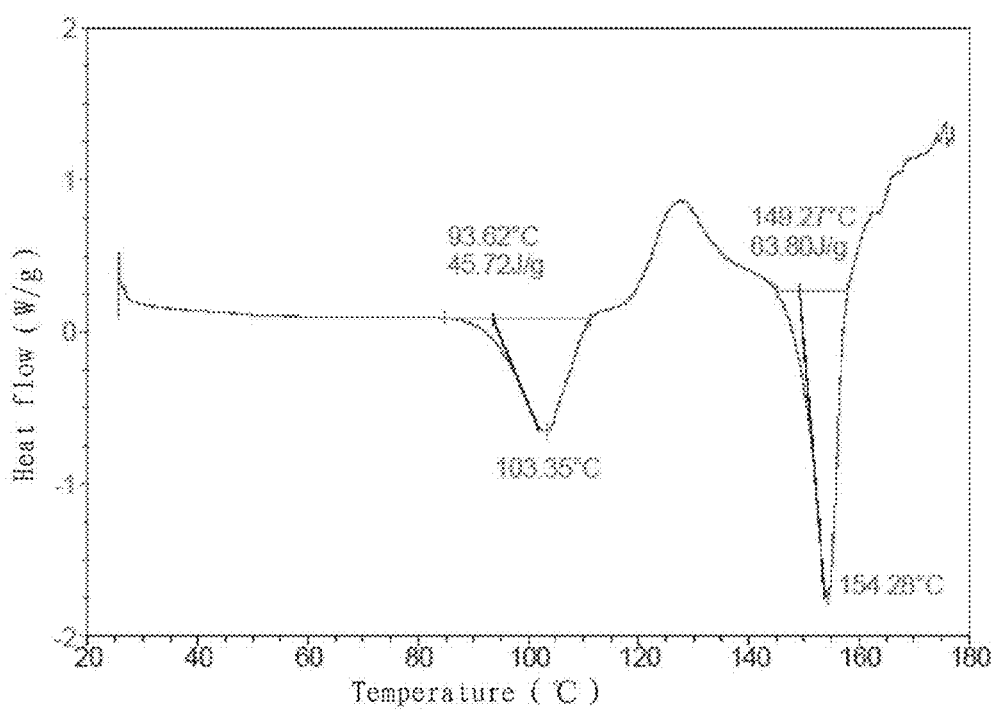
FIG. 14 is the DSC thermogram of the crystal form G.

The X-ray powder diffraction analysis (XRPD), thermogravimetric analysis (TGA) and differential thermal analysis (DSC) of the crystal form G are shown in FIGS. 12-14.

Figure 15:
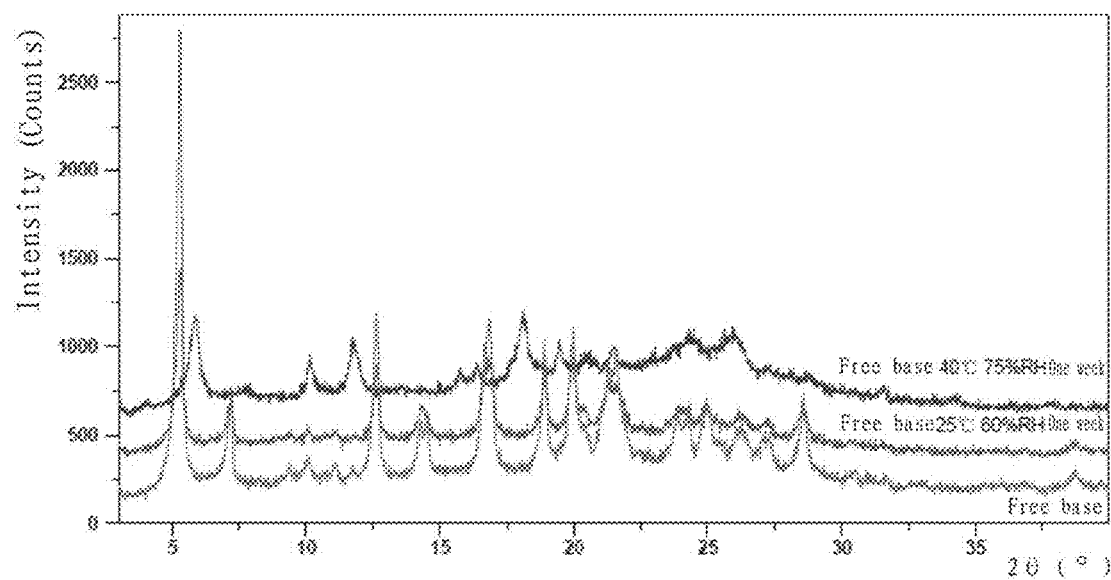
FIG. 15 is the comparison chart of the XRPD patterns of the free base of the compound of formula I after preparation, after one week of storage under the condition of 25° C./60% R.H., after one week of storage under the condition of 40° C./75% R.H.

Test Example 1 Storage Stability Test of the Free Base, the Crystal Form K, and the Crystal Form F of the Compound of Formula I After one week of storage of the free base of the compound of formula I under the conditions of 25° C./60% R.H. and 40° C./75% R.H., the XRPD patterns of the free base changed significantly (FIG. 15), showing that the crystal form of the free base of the compound of formula I was less stable and was not suitable as drug substance for drug product preparation.

Figure 16:
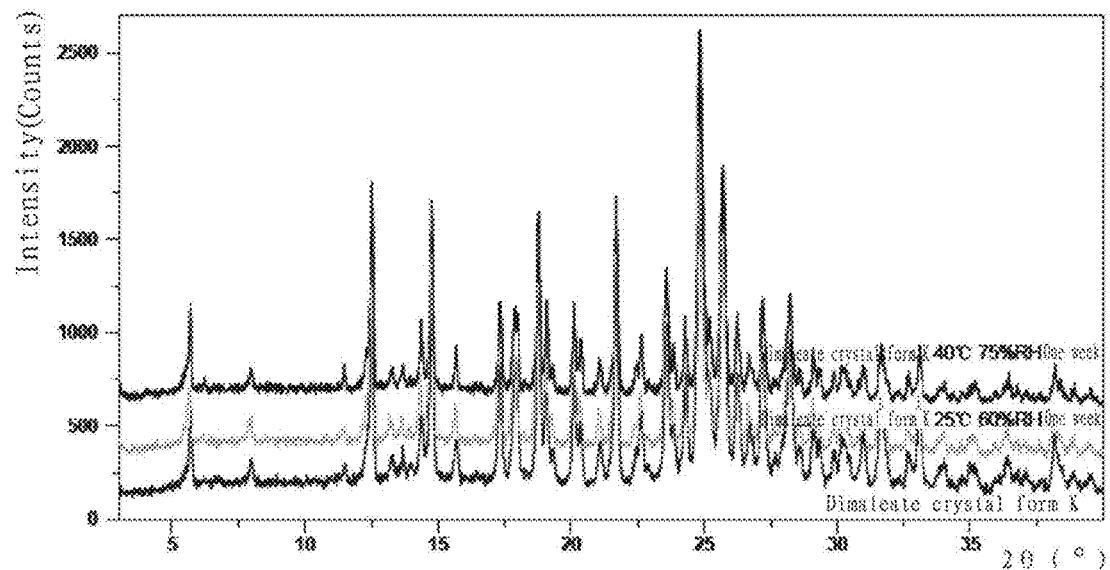
FIG. 16 is the comparison chart of the XRPD patterns of the crystal form K of the compound of formula I after preparation, after one week of storage under the condition of 25° C./60% R.H., after one week of storage under the condition of 40° C./75% R.H.
Figure 17:
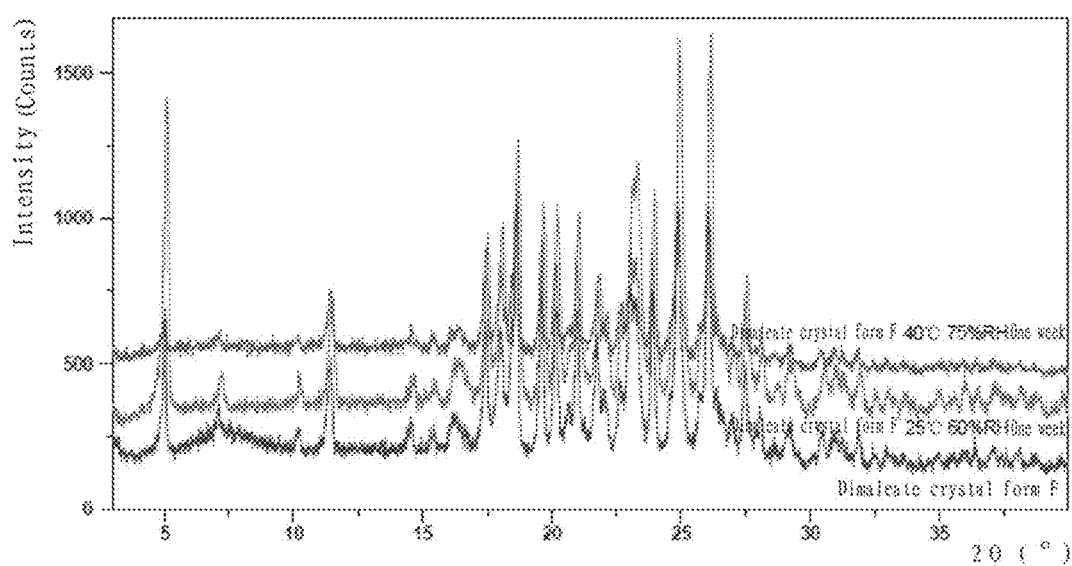
FIG. 17 is the comparison chart of the XRPD patterns of the crystal form F of the compound of formula I after preparation, after one week of storage under the condition of 25° C./60% R.H., after one week of storage under the condition of 40° C./75% R.H.

After one week of storage of the crystal form K and the crystal form F under the conditions of 25° C./60% R.H. and 40° C./75% RH., the XRPD patterns of the crystal form K and crystal form F are basically the same, as shown in FIGS. 16 and 17, respectively, showing that the crystal form K and the crystal form F are stable for at least one week under the conditions of 25° C./60% R.H. and 40° C./75% R.H.

The above experiments showed that the crystal form K and the crystal form F of the compound of formula I have better physical stability than the free base of the compound of formula I.

After one week of storage of the free base of the compound of formula I under the condition of 40° C./75% R.H., according to HPLC measurement, the chemical content decreased to 94.8% of the initial content, indicating that the chemical stability was poor.

After one week of storage of the crystal form K, the crystal form E, the crystal form F and the crystal form G under the condition of 40° C./75% R.H., according to HPLC measurement, the chemical contents were stable, indicating that the four crystal forms have good chemical stability.

The results are summarized in Table 3.

TABLE 3

|  | Initial content | 25° C./60% R.H. One week Chemical stability | 40° C./75% R.H. One week Chemical stability |
| --- | --- | --- | --- |
| Free base | 100.0% | 99.8% | 94.8% |
| Crystal form K | 100.0% | 99.9% | 99.8% |
| Crystal form E | 100.0% | 99.8% | 99.5% |
| Crystal form F | 100.0% | 99.8% | 99.7% |
| Crystal form G | 100.0% | 99.8% | 99.6% |

Figure 18:
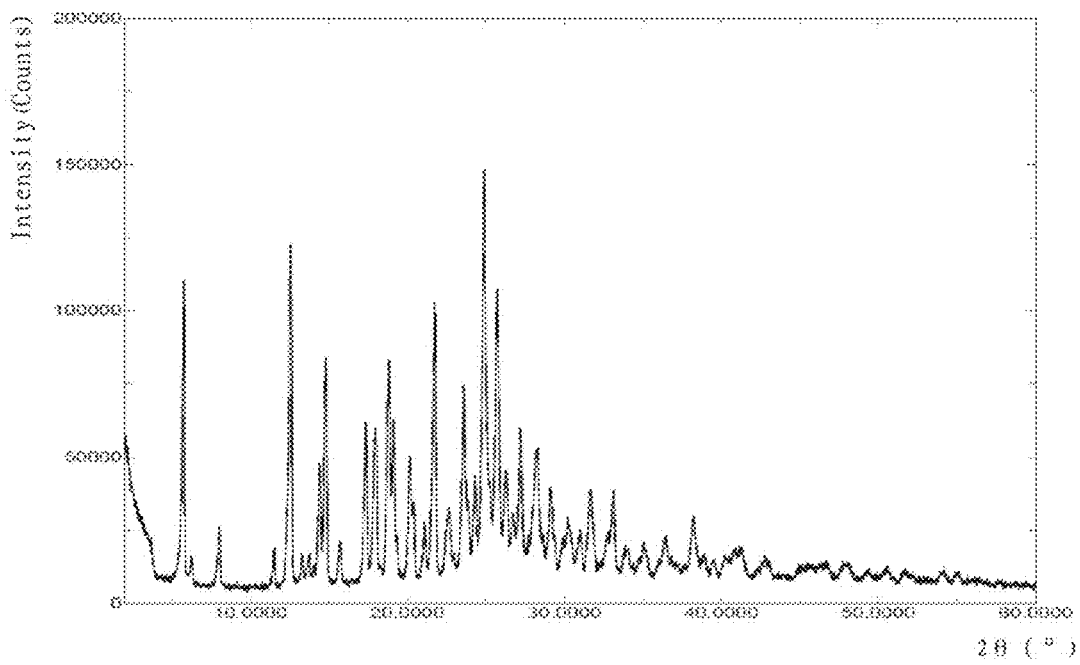
FIG. 18 is the XRPD pattern of the crystal form K of the compound of formula I after six months of storage under the condition of 40° C./75% R.H.

After 6 months of storage of the crystal form K under the condition of 40° C./75% R.H., the XRPD pattern was basically the same, as shown in FIG. 18, indicating that the crystal form K has good physical and chemical stability.

Figure 19:
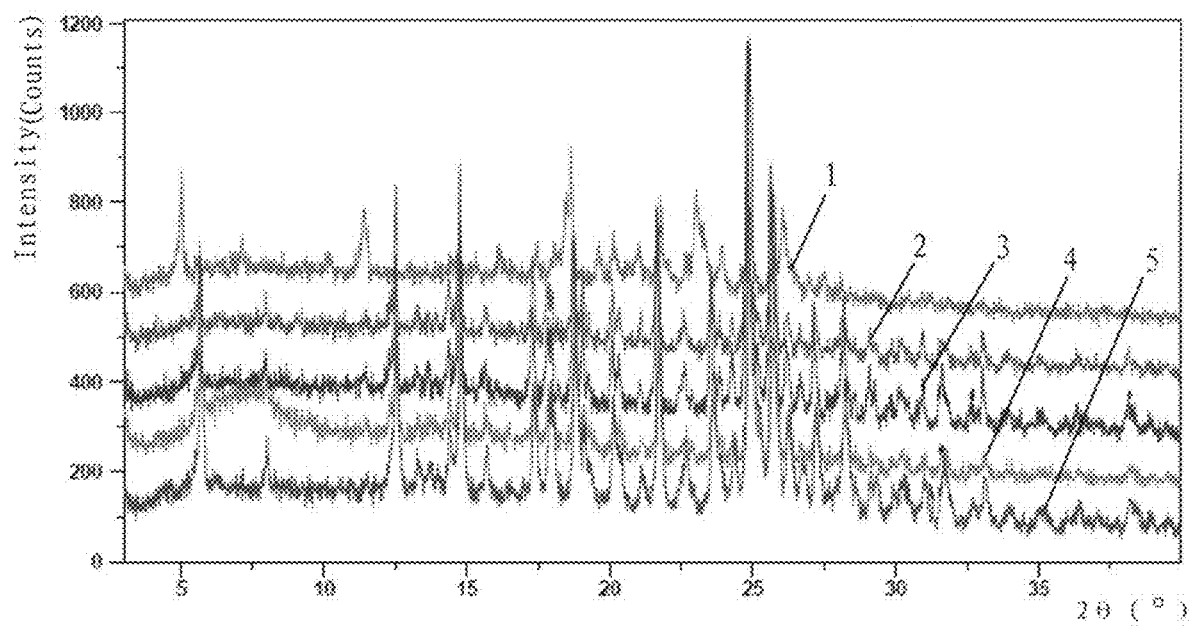
FIG. 19 is the experiment result of the competition of stability between crystal form K and crystal form F of the compound of formula I in test example 2, wherein patterns 1-5 show the XRPD patterns of the samples numbered 1-5 in test example 2 respectively.

Test Example 2 the First Set of Comparative Tests of the Competition of Stabilities Between the Crystal Form K and the Crystal Form F Approximately 10 mg of crystal form K was weighed and was added to the saturated solutions (with different water activities) of crystal form K to form suspensions, then the crystal form F was added (about 10 mg). After 12 hours of stirring under room temperature, the solid was isolated by centrifugation and the XRPD thereof was tested. The results are summarized in Table 4 and FIG. 19. It can be seen from the results that under room temperature, when the water activity was greater than or equal to 0.15, the crystal form K was thermodynamically more stable than the crystal form F.

TABLE 4

| Sample No. | Water activity | Solvent:water | Crystal form |
|---|---|---|---|
| 1 | 0.00 | IPA | Crystal form F |
| 2 | 0.15 | IPA:H$_2$O 99:1 | Crystal form K |
| 3 | 0.39 | IPA:H$_2$O 24:1 | Crystal form K |
| 4 | 0.60 | ACN:H$_2$O 19:1 | Crystal form K |
| 5 | 0.80 | ACN:H$_2$O 9:1 | Crystal form K |

Test Example 3 the Second Set of Comparative Tests of the Competition of Stabilities Between the Crystal Form K and the Crystal Form F Approximately 10 mg of crystal form F was weighed and about 0.1 mg crystal form K was added thereto, they were mixed under oscillation. Then two samples were placed in different environments for 10 days and were subjected to XRPD test respectively. The results are summarized in Table 5.

TABLE 5

| Sample No. | Crystal form F (mg) | Crystal form K (mg) | Temperature (° C.) | Humidity (% R.H) | Time (day) | Crystal form |
|---|---|---|---|---|---|---|
| 1 | 7.89 | 0.08 | 25 | 60 | 10 | Crystal form F |
| 2 | 12.016 | 0.12 | 40 | 75 | 10 | Crystal form K |

As can be seen from the results, under the condition of 40° C./75% R.H., when there's crystal form K, the crystal form F was converted to the crystal form K, i.e. at this time, the crystal form K has better thermodynamic stability than the crystal form F.

Under the condition of 25° C./60% RH., when there's crystal form K, the crystal form F did not in change, indicating that the crystal form F has good dynamic stability under the condition of 25° C./60% RH.

Test Example 4 Comparative Test of the Storage Stability Between the Crystal Form K and the Crystal Form G Approximately 10 mg of crystal form K was weighed and was added to the saturated water solution of crystal form K to form a suspension, then the crystal form G was added (about 10 mg).

Figure 20:
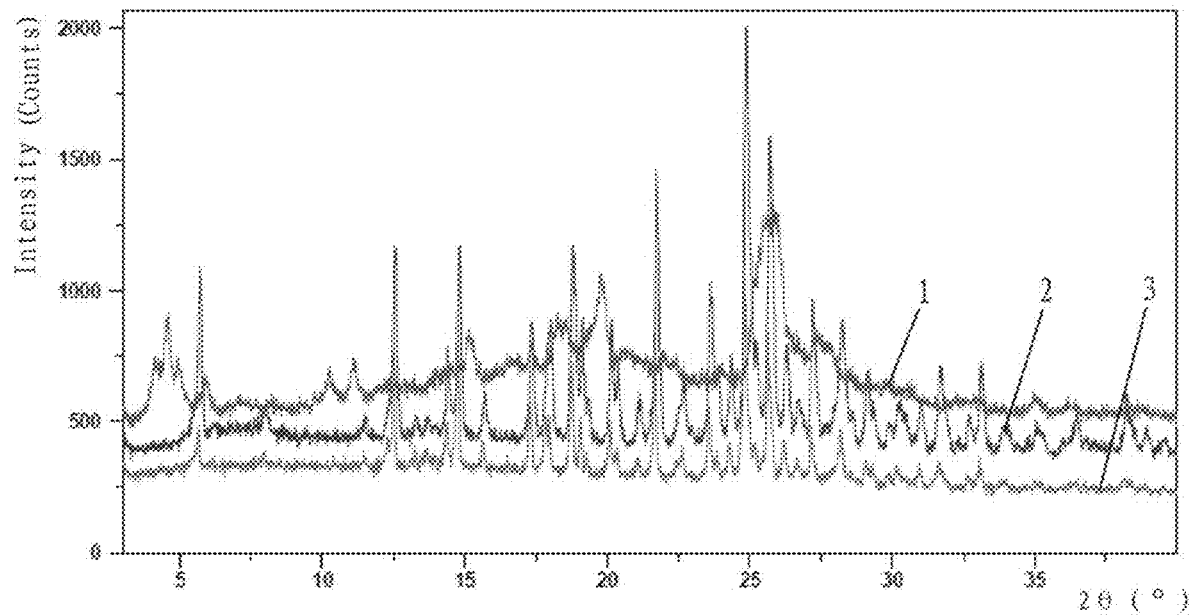
FIG. 20 is the experiment result of the competition of stability between crystal form K and crystal form G of the compound of formula I in test example 4, wherein pattern 1 is the XRPD pattern of the crystal form G pattern 2 is the XRPD pattern of the crystal form K, and pattern 3 is the XRPD pattern of the crystal after the test of the competition of the crystal stability.

After 12 hours of stirring under room temperature, the solid was separated by centrifugation and was subjected to XRPD test, the results are shown in FIG. 20.

As can be seen from the results, the crystal form G was converted to crystal form K under the condition of room temperature. Therefore, under room temperature, the crystal form K was thermodynamically more stable than the crystal form G in water.

Test Example 5 Solubility of the Free Base, the Crystal Form K and the Crystal Form F of the Compound of Formula I The solubility of the free base, the crystal form K and the crystal form F of the compound of formula I under different pH conditions, in water, fasted state simulated intestinal fluid (FaSSIF), fed state simulated intestinal fluid (FeSSIF) and simulated gastric fluid (SGF) were tested. Wherein FaSSIF and FeSSIF were prepared according to the method described in the literature: Study of a Standardized Taurocholate-Lecithin Powder for Preparing the Biorelevant Media FeSSIF and FaSSIF (Kloefer, B., van Hoogevest, P., Moloney, R., Kuentz, M., Leigh, M. L., & Dressman, J. (2010). Dissolution Technologies, Aug. 17(3), 6-14. SGF was prepared according to the method described in the literature Albendazole Generics-A Comparative In Vitro Study (Galia E., Horton, J and Dressman J. (1999) Pharmaceutical Research, 16 (12), 1871-1975). The test results are summarized in Table 6.

TABLE 6

| | | Solubility (mg/mL) | | |
|---|---|---|---|---|
| Medium | pH value | Free base | Crystal form K | Crystal form F |
| Water | 7.4 | <0.0025 | >10.02 | >9.81 |
| FaSSIF | 6.5 | 0.03 | 8.36 | 2.44 |
| FeSSIF | 5.0 | 0.10 | 1.24 | 0.57 |
| SGF | 1.8 | 8.37 | >9.95 | >10.65 |

The invention claimed is:

1. A crystal form E of the dimaleate of the compound of Formula I,

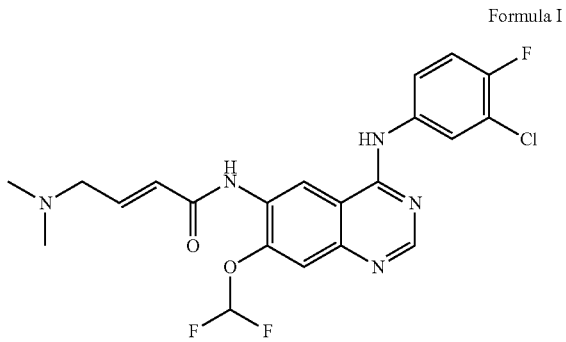 [SMILES: CN(C)C/C=C/C(=O)Nc1cc2c(Nc3ccc(F)c(Cl)c3)ncnc2cc1OC(F)F]

Formula I wherein the X-ray powder diffraction pattern (CuKα radiation) of the crystal form E comprises characteristic peaks at the following diffraction angles 2θ: 4.5±0.2°, 12.0±0.2°, 18.2±0.2°, 19.8±0.2°, 20.6±0.2°, 21.9±0.2°, 24.7±0.2°, and 25.3±0.2°.

2. The crystal form E according to claim 1, characterized in that the relative intensities of the characteristic peaks are:

| diffraction angles 2θ | relative intensities (%) |
|---|---|
| 4.5 ± 0.2° | 26.3 |
| 12.0 ± 0.2° | 14.1 |
| 18.2 ± 0.2° | 82.3 |
| 19.8 ± 0.2° | 31.2 |
| 20.6 ± 0.2° | 27.7 |
| 21.9 ± 0.2° | 50.8 |
| 24.7 ± 0.2° | 34.5 |
| 25.3 ± 0.2° | 100.0. |

3. A crystal form F of the dimaleate of the compound of Formula I,

Formula I

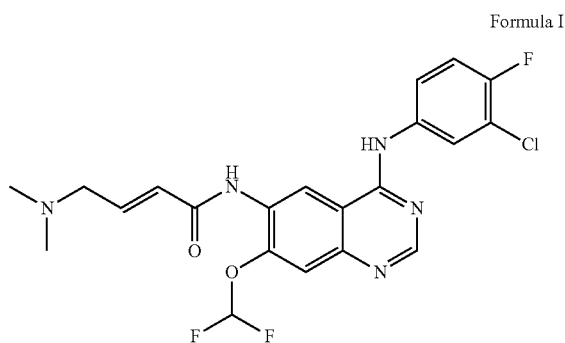 [SMILES: CN(C)C/C=C/C(=O)Nc1cc2c(Nc3ccc(F)c(Cl)c3)ncnc2cc1OC(F)F]

wherein the X-ray powder diffraction pattern (CuKα radiation) of the crystal form F comprises characteristic peaks at the following diffraction angles 2θ: 5.1±0.2°, 11.5±0.2°, 17.5±0.2°, 18.7±0.2°, 19.7±0.2°, 23.3±0.2°, 25.0±0.2°, and 26.2±0.2°.

4. The crystal form F according to claim 3, characterized in that the relative intensities of the characteristic peaks are:

| diffraction angles 2θ | relative intensities (%) |
|---|---|
| 5.1 ± 0.2° | 100.0 |
| 11.5 ± 0.2° | 20.5 |
| 17.5 ± 0.2° | 14.2 |
| 18.7 ± 0.2° | 42.8 |
| 19.7 ± 0.2° | 22.5 |
| 23.3 ± 0.2° | 31.0 |
| 25.0 ± 0.2° | 44.6 |
| 26.2 ± 0.2° | 42.1. |

5. A crystal form G of the dimaleate of the compound of Formula I,

Formula I

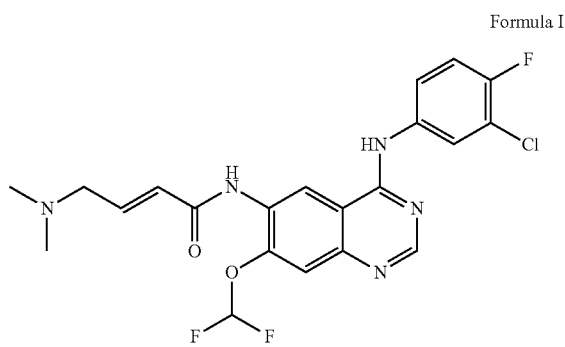 [SMILES: CN(C)C/C=C/C(=O)Nc1cc2c(Nc3ccc(F)c(Cl)c3)ncnc2cc1OC(F)F]

wherein the X-ray powder diffraction pattern (CuKα radiation) of the crystal form G comprises characteristic peaks at the following diffraction angles 2θ: 4.5±0.2°, 10.1±0.2°, 15.1±0.2°, 18.5±0.2°, 25.8±0.2°.

6. The crystal form G according to claim 5, characterized in that the relative intensities of the characteristic peaks are:

| diffraction angles 2θ | relative intensities (%) |
|---|---|
| 4.5 ± 0.2° | 28.8 |
| 10.1 ± 0.2° | 19.5 |
| 15.1 ± 0.2° | 13.2 |
| 18.5 ± 0.2° | 38.1 |
| 25.8 ± 0.2° | 100.0. |

7. A composition comprising the crystal form E of the dimaleate of the compound of Formula I according to claim 1.

8. A composition comprising the crystal form F of the dimaleate of the compound of Formula I according to claim 3.

9. A composition comprising the crystal form G of the dimaleate of the compound of Formula I according to claim 5.

10. A method for treating indications associated with EGFR and HER2 kinase function, the method comprising:
administering the crystal form E of the dimaleate of the compound of Formula I according to claim 1;
wherein the indication associated with EGFR and HER2 kinase function is selected from the group consisting of breast cancer, ovarian cancer, gastrointestinal cancer, esophageal cancer, lung cancer, head and neck squamous cell carcinoma, pancreatic cancer, epidermal squamous carcinoma, prostate cancer, glioma, nasopharyngeal cancer and combinations thereof.

11. A method for treating indications associated with EGFR and HER2 kinase function, the method comprising:
administering the crystal form F of the dimaleate of the compound of Formula I according to claim 3;
wherein the indication associated with EGFR and HER2 kinase function is selected from the group consisting of breast cancer, ovarian cancer, gastrointestinal cancer, esophageal cancer, lung cancer, head and neck squamous cell carcinoma, pancreatic cancer, epidermal squamous carcinoma, prostate cancer, glioma, nasopharyngeal cancer and combinations thereof.

12. A method for treating indications associated with EGFR and HER2 kinase function, the method comprising:
administering the crystal form G of the dimaleate of the compound of Formula I according to claim 5;
wherein the indication associated with EGFR and HER2 kinase function is selected from the group consisting of breast cancer, ovarian cancer, gastrointestinal cancer, esophageal cancer, lung cancer, head and neck squamous cell carcinoma, pancreatic cancer, epidermal squamous carcinoma, prostate cancer, glioma, nasopharyngeal cancer and combinations thereof.

* * * * *